United States Patent
Aldayel

(10) Patent No.: US 12,083,156 B1
(45) Date of Patent: Sep. 10, 2024

(54) EXTRACTS DERIVED FROM LASER-IRRADIATED RHIZOME OF CURCUMA LONGA HAVING ENHANCED ANTIMICROBIAL ACTIVITY

(71) Applicant: KING FAISAL UNIVERSITY, Al-Ahsa (SA)

(72) Inventor: Munirah Fahad Aldayel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/517,708

(22) Filed: Nov. 22, 2023

Related U.S. Application Data

(63) Continuation of application No. 18/136,732, filed on Apr. 19, 2023, now abandoned.

(51) Int. Cl.
| | |
|---|---|
| *A61K 36/9066* | (2006.01) |
| *A61K 31/015* | (2006.01) |
| *A61K 31/12* | (2006.01) |
| *A61K 36/00* | (2006.01) |
| *A61P 31/06* | (2006.01) |

(52) U.S. Cl.
CPC ........ *A61K 36/9066* (2013.01); *A61K 31/015* (2013.01); *A61K 31/12* (2013.01); *A61P 31/06* (2018.01); *A61K 2236/11* (2013.01); *A61K 2236/33* (2013.01)

(58) Field of Classification Search
None
See application file for complete search history.

(56) References Cited

U.S. PATENT DOCUMENTS 6,497,908 B1 * 12/2002 Oshiro ............... A23D 9/02
426/601

OTHER PUBLICATIONS

Hoang Van Nong et al. ("Fabrication and vibration characterization of curcumin extracted from turmeric (*Curcuma longa*) rhizomes of the northern Vietnam", Van Nong et al. SpingerPlus (2016) 5:1147, pp. 1-9) (Year: 2016).*

The EM spectrum (See website article, labman.phys.utk.edu/phys222core/modules/m6/The EM spectrum.html, Mar. 6, 2024, pp. 1-3). (Year: 2024).*

Trigo-Gutierrez et al., "Antimicrobial Activity of Curcumin in Nanoformulations: A Comprehensive Review," Int J Mol Sci. Jul. 2021; 22(13): 7130.

Yang et al., "Low-dose blue light irradiation enhances the antimicrobial activities of curcumin against Propionibacterium acnes," Journal of Photochemistry and Photobiology B: Biology, vol. 189, Dec. 2018, pp. 21-28.

Seong et al., "Curcumin Mitigates Accelerated Aging after Irradiation in *Drosophila* by Reducing Oxidative Stress," Biomed Res Int. 2015; 2015: 425380.

Mahesh et al., "Effect of Photo-Irradiated Curcumin Treatment Against Oxidative Stress in Streptozotocin-Induced Diabetic Rats," Journal of Medicinal Food, vol. 8, No. 2, Jul. 20, 2005.

Chosdu et al., "The effect of gamma irradiation on curcumin component of Curcuma domestica," Radiation Physics and Chemistry, vol. 46, Issues 4-6, Part 1, Oct.-Dec. 1995, pp. 663-667.

* cited by examiner

*Primary Examiner* — Aaron J Kosar
*Assistant Examiner* — Randall O Winston
(74) *Attorney, Agent, or Firm* — Nath, Goldberg & Meyer; Joshua B. Goldberg

(57) ABSTRACT

Methods of producing, compositions containing, and methods for administering curcumin, and particularly extracts obtained from a laser irradiated rhizome of *Curcuma longa* having an enhanced antimicrobial activity. An ethanolic extract of the laser irradiated rhizome of *Curcuma longa* exhibits increased levels of bisdemethoxycurcumin and curcumin, as well as of alpha-curcumene, (-)-zingiberene, caryophyllene, and beta sesquiphellandrene as compared to those of an ethanolic extract from a *Curcuma longa* rhizome not irradiated by a laser.

6 Claims, No Drawings

EXTRACTS DERIVED FROM LASER-IRRADIATED RHIZOME OF CURCUMA LONGA HAVING ENHANCED ANTIMICROBIAL ACTIVITY

CROSS-REFERENCE TO RELATED APPLICATION

This application is a continuation of U.S. patent application Ser. No. 18/136,732, filed on Apr. 19, 2023, the entire contents of which are incorporated herein by reference.

BACKGROUND

Field

The disclosure of the present patent application relates to methods of producing, compositions containing, and methods for administering curcumin, and particularly to extracts obtained from a laser irradiated rhizome of *Curcuma longa* having an enhanced antimicrobial activity.

Description of the Prior Art

Curcumin, a polyphenol derived from the rhizome of turmeric (*Curcuma longa* L. (Zingiberaceae)) is characterized by a comprehensive range of biological, medicinal, and pharmacological activities. Curcumin has been demonstrated to have antioxidant, antimicrobial, anti-malarial, anticancer, anti-thrombotic, anti-hyperlipidemic, hypoglycemic, anti-inflammatory, anti-rheumatic, and myocardial infarction protective activities. Although it is efficacious and safe, Curcumin has not been widely used as a therapeutic agent, mainly for problems related to its poor bioavailability and solubility. Pharmacokinetic studies of curcumin have exhibited poor absorption, fast metabolism, and fast elimination as major reasons for its poor bioavailability.

*Curcuma longa* is used traditionally as a spice and natural yellow colorant in food. In additional to its culinary usage, it also exhibits many medicinal values such as antimicrobial, anti-inflammatory, antioxidant, anticarcinogenic, antidiabetic, antidepressant, and hepatoprotective properties, as well as effectiveness in prevention of cardiovascular diseases and treatment of several gastrointestinal disorders. The active compounds in turmeric are flavonoids and various volatile oils. The most abundant flavonoid in *C. longa* is referred to as curcuminoid, which is composed of 3 major components, namely the curcumin (diferuloylmethane), bis-demethoxycurcumin, and demethoxycurcumin.

Laser irradiation of seeds has been reported to enhance plant growth of seedlings of several plant species.

Thus, compositions and methods to solve the aforementioned problems are desired.

SUMMARY OF THE INVENTION

The present subject matter relates to methods of producing, compositions containing, and methods for administering curcumin, and particularly to extracts obtained from a laser irradiated rhizome of *Curcuma longa* having an enhanced antimicrobial activity, particularly against multidrug resistant bacteria.

Accordingly, in one embodiment, the present subject matter relates to a method of enhancing active components in *Curcuma longa*, the method comprising: providing a *Curcuma longa* rhizome; irradiating the *Curcuma longa* rhizome with a laser; and obtaining a modified *Curcuma longa* rhizome having an enhanced concentration of active components. In another embodiment, the present methods can further comprise obtaining an ethanolic extract of the modified *Curcuma longa* rhizome.

In another embodiment, the present subject matter relates to a *Curcuma longa* ethanolic extract produced according to the methods as described herein.

In a further embodiment, the present subject matter relates to a therapeutically effective composition comprising a therapeutically effective amount of the *Curcuma longa* ethanolic extract as described herein and a therapeutically acceptable carrier.

In one more embodiment, the present subject matter relates to a method of treating a bacterial infection in a patient, comprising administering to a patient in need thereof a therapeutically effective amount of the *Curcuma longa* ethanolic extract as obtained herein.

These and other features of the present subject matter will become readily apparent upon further review of the following specification.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

"Subject" or "patient" as used herein refers to any animal classified as a mammal, including humans, domestic and farm animals, and zoo, sports, and pet companion animals such as household pets and other domesticated animals such as, but not limited to, cattle, sheep, ferrets, swine or pigs, horses, camels, poultry, rabbits, goats, dogs, cats, and the like.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to methods of producing, compositions containing, and methods for administering curcumin, and particularly to extracts obtained from a laser irradiated rhizome of *Curcuma longa* having an enhanced antimicrobial activity, particularly against multi-drug resistant bacteria.

Accordingly, in one embodiment, the present subject matter relates to a method of enhancing active components in *Curcuma longa*, the method comprising: providing a *Curcuma longa* rhizome; irradiating the *Curcuma longa* rhizome with a laser; and obtaining a modified *Curcuma longa* rhizome having an enhanced concentration of active components. In another embodiment, the present methods can further comprise obtaining an ethanolic extract of the modified *Curcuma longa* rhizome.

In an embodiment, the *Curcuma longa* rhizome is irradiated with a laser having a wavelength of about 632 nm and a density power of about 5.5 mW/mm$^2$. In this regard, the laser can be a red laser. In another embodiment, the laser can be a Helium-Neon (HeNe) laser. Other, similar lasers are further contemplated for use herein. For example, other red lasers having a similar wavelength but a different power can potentially be used herein, for example, lasers having a density power of about 0.8 mW/mm$^2$ to about 22.5 mW/mm$^2$.

In another embodiment, the laser can be about 20 to about 60 mm from the *Curcuma longa* rhizome during the irradiation step. In one non-limiting embodiment in this regard, the laser can be about 40 mm from the *Curcuma longa* rhizome during the irradiation step.

In a further embodiment, the *Curcuma longa* rhizome can be irradiated for about 1 to about 15 minutes. By way of non-limiting example, the *Curcuma longa* rhizome can be irradiated for about 10 or about 15 minutes. In other embodiments, the *Curcuma longa* rhizome can be irradiated for more than about 15 minutes.

In certain embodiments, the ethanolic extract of the modified *Curcuma longa* rhizome can have about 101 μg/mL of bisdemethoxycurcumin, about 70 μg/mL of demethoxycurcumin, and about 380 μg/mL of curcumin. These levels of bisdemethoxycurcumin and curcumin can be increased over those observed in an untreated *Curcuma longa* rhizome, while the level of demethoxycurcumin can be decreased over that observed in an untreated *Curcuma longa* rhizome.

In a similar embodiment, the ethanolic extract of the modified *Curcuma longa* rhizome can have at least an about 1.67-fold increase in alpha-curcumene as compared to that of an untreated *Curcuma longa* rhizome. Likewise, the ethanolic extract of the modified *Curcuma longa* rhizome can have increased amounts of alpha-curcumene, (-)-zingiberene, caryophyllene, and beta sesquiphellandrene as compared to those of an untreated *Curcuma longa* rhizome. In contrast, the laser ray treatments provided herein can cause a decrease in the amount of ar-turmerone and beta-turmerone as compared with those of an untreated *Curcuma longa* rhizome.

In another embodiment, the present subject matter relates to a *Curcuma longa* ethanolic extract produced according to the methods as described herein.

In certain embodiments, the *Curcuma longa* ethanolic extract as described herein can have about 101 μg/mL of bisdemethoxycurcumin, about 70 μg/mL of demethoxycurcumin, and about 380 μg/mL of curcumin. These levels of bisdemethoxycurcumin and curcumin can be increased over those observed in an ethanolic extract from an untreated *Curcuma longa* rhizome, while the level of demethoxycurcumin can be decreased over that observed in an ethanolic extract from an untreated *Curcuma longa* rhizome.

In a similar embodiment, the *Curcuma longa* ethanolic extract as described herein can have at least an about 1.67-fold increase in alpha-curcumene as compared to that of an untreated *Curcuma longa* rhizome. Likewise, the *Curcuma longa* ethanolic extract can have increased amounts of alpha-curcumene, (-)-zingiberene, caryophyllene, and beta sesquiphellandrene as compared to those of an ethanolic extract from an untreated *Curcuma longa* rhizome. In contrast, the *Curcuma longa* ethanolic extracts provided herein can have decreased amounts of ar-turmerone and beta-turmerone as compared with those of an untreated *Curcuma longa* rhizome.

In a further embodiment, the present subject matter relates to a therapeutically effective composition comprising a therapeutically effective amount of the *Curcuma longa* ethanolic extract as described herein and a therapeutically acceptable carrier.

In an embodiment, the compositions described herein can be prepared by mixing the *Curcuma longa* ethanolic extracts described herein with an orally acceptable carrier. For example, the method of making a composition herein can include mixing the *Curcuma longa* ethanolic extracts described herein with an orally acceptable carrier with preservatives, buffers, and/or propellants to create the composition. Carriers are inert pharmaceutical excipients, including, but not limited to, binders, suspending agents, lubricants, flavorings, sweeteners, preservatives, dyes, and coatings. In preparing compositions in oral dosage form, any of the carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, sterile parenteral solutions or suspensions, metered aerosol or liquid sprays, drops, ampules, for oral administration. The composition can be presented in a form suitable for daily, weekly, or monthly administration. The compositions herein will contain, per dosage unit, e.g., tablet, capsule, powder, and the like, amounts of the active ingredients necessary to deliver an effective dose. Effective amounts of the *Curcuma longa* ethanolic extracts described herein may be determined initially from the Examples described herein and adjusted for specific targeted diseases using routine methods.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a therapeutically acceptable non-toxic composition may be formed by the incorporation of any normally employed excipients, such as, for example, pharmaceutical grades of mannitol, lactose, starch, magnesium stearate, talcum, cellulose derivatives, sodium cross-carmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the compositions as described herein in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of therapeutically effective composition contained in such parenteral compositions is highly dependent on the specific nature thereof, as well as the activity of the composition and the needs of the subject.

The present compositions may have valuable pharmaceutical properties, which make them commercially utilizable.

Accordingly, the present subject matter further relates to use of the present compositions for the treatment of diseases or infections, especially bacterial infections.

In this regard, the present subject matter relates to a method of treating a bacterial infection in a patent, comprising administering to a patient in need thereof a therapeutically effective amount of the *Curcuma longa* ethanolic extract as obtained herein.

In this regard, the bacterial infection treatable herein can be caused by *S. aureus, E. coli*, MRSA, or *Bacillus* sp. In other embodiments, the bacterial infection can be caused by a multi-drug resistant bacterium. In further embodiments, the administration of the *Curcuma longa* ethanolic extract can eliminate bacteria causing the bacterial infection.

In certain embodiments in this regard, other treatment methods are further contemplated herein. Certain non-limiting exemplary diseases, disorders, and conditions potentially treatable by the present compositions in this regard include oxidative and inflammatory conditions, metabolic syndrome, arthritis, anxiety, hyperlipidemia, exercise-induced inflammation and muscle soreness, pain, kidney diseases, inflammatory and degenerative eye conditions, and any combination thereof.

Further contemplated within the present methods are generating an anti-inflammatory and antioxidant effect in a subject receiving the presently described compositions.

The present subject matter also relates to the use of a composition as described herein in the manufacture of a pharmaceutical composition for the treatment of bacterial infections, such as the diseases or disorders exemplified above. In particular, the present subject matter relates to the use of a composition as described herein in the manufacture of a therapeutically effective composition for the treatment or prophylaxis of bacterial infections, such as, but not limited to, bacterial infections caused by caused by *S. aureus, E. coli*, MRSA, *Bacillus* sp., or any combination thereof.

The present subject matter further relates to a method of treating or preventing a disease comprising administering to a patient in need thereof a therapeutically effective amount of at least one of the compositions herein.

In particular, the present subject matter relates to a method of treating one of the above-mentioned diseases or disorders comprising administering to a patient in need thereof a therapeutically effective amount of at least one of the compositions herein.

In the above methods, the patient is preferably a mammal, more preferably a human.

The following examples relate to various methods of manufacturing or using certain specific compositions as described herein.

EXAMPLES

Example 1

A *Curcuma longa* rhizome was placed in a petri dish and irradiated with a laser ray from 40 mm from the rhizome for 10- and 15 min., respectively. The laser radiation used had a 632 nm wavelength, and a density power of 5.5 mW/mm$^2$.

Following GC-MS analysis, at least 10 components were discovered in the ethanolic extracts of the *C. longa* rhizomes. Table 1 lists the names of the compounds and their retention times (RTs), peak areas (in percentage), molecular formulae, and molecular weights. The effects of laser ray on the composition of alpha-curcumene, (-)-zingiberene, beta-sesquiphellandrene, aromatic turmerone (ar-turmerone), beta-turmerone, and caryophyllene are displayed in Table (1). Substantial amounts of alpha-curcumene (-)-zingiberene, beta-sesquiphellandrene, aromatic turmerone (ar-turmerone) and beta-turmerone were present in the extracts of all treatments. These five components have been identified as the major components of *C. longa* essential oil. The application of 10 min Laser ray resulted in an approximately 1.67 fold increase in alpha-curcumene compared to the control. Laser ray concentrations (10 and 15 min) caused an increase in the levels of (-)-zingiberene and beta-sesquiphellandrene as compared to control (Table 1). On the other hand, the Laser ray treatments caused a decrease in the amount of ar-turmerone and beta-turmerone as compared with the control treatment. Caryophyllene was found in the Laser ray treatment groups, the 10 min laser treatment resulted in an increase in caryophyllene content (Table 1).

TABLE 1

Components identified by GC-MS analysis in the C. longa ethanolic rhizome extracts from different treatment groups. Each area (%) was calculated from the measurements obtained frin the ethanolic extracts of 3 replicates.

| Laser treatment (min) | Peak | Essential oils compounds | RT, min | Area, % | Molecular Weight | Molecular formula |
|---|---|---|---|---|---|---|
| | 1 | Curcumene | 14.471 | 4.65 | 202.33 | C15H22 |
| | 2 | (−)-Zingiberene | 14.641 | 25.03 | 204.35 | C15H24 |
| Control | 3 | beta-Bisabolene | 14.808 | 3.66 | 204.35 | C15H24 |
| | 4 | (−)-.beta.-Sesquiphellandrene | 15.021 | 21.54 | 204.35 | C15H24 |
| | 5 | 4-(2,2-Dimethyl-6-methylenecyclohexyl)butanal | 16.123 | 1.5 | 194.3132 | C13H22O |
| | 6 | ar-Turmerone | 16.683 | 4.82 | 216.32 | C15H20O |
| | 7 | Tumerone | 16.74 | 21.8 | 218.3346 | C15H22O |
| | 8 | Cyclopentane | 17.132 | 12.23 | 70.13 | C5H10 |
| | 9 | Tricyclo | 17.472 | 2.22 | 204.35 | C15H24 |
| | 10 | Cyclohexane, 1-methyl-2,4-bis(1-methylethenyl)- | 18.067 | 2.55 | 204.35 | C15H24 |

TABLE 1-continued

Components identified by GC-MS analysis in the C. longa ethanolic rhizome extracts from different treatment groups. Each area (%) was calculated from the measurements obtained frin the ethanolic extracts of 3 replicates.

| Laser treatment (min) | Peak | Essential oils compounds | RT, min | Area, % | Molecular Weight | Molecular formula |
|---|---|---|---|---|---|---|
| 10 min | 1 | Curcumene | 14.472 | 5.43 | 202.33 | C15H22 |
| | 2 | (−)-Zingiberene | 14.643 | 30.03 | 204.35 | C15H24 |
| | 3 | beta-Bisabolene | 14.81 | 4.31 | 204.35 | C15H24 |
| | 4 | (−)-.beta.-Sesquiphellandrene | 15.023 | 23.72 | 204.35 | C15H24 |
| | 5 | 4-(2,2-Dimethyl-6-methylenecyclohexyl)butanal | 16.127 | 1.32 | 194.3132 | C13H22O |
| | 6 | ar-Turmerone | 16.688 | 2.81 | 216.32 | C15H20O |
| | 7 | Turnerone | 16.744 | 17.79 | 218.3346 | C15H22O |
| | 8 | Caryophyllene | 17.136 | 10.68 | 204.36 | C15H24 |
| | 9 | Cyclopentane | 17.482 | 1.97 | 70.13 | C5H10 |
| | 10 | Cyclohexane, 1-methyl-2,4-bis(1-methylethenyl)- | 18.07 | 1.94 | 204.35 | C15H24 |
| 15 min | 1 | Curcumene | 14.474 | 4.86 | 202.33 | C15H22 |
| | 2 | (−)-Zingiberene | 14.643 | 33.82 | 204.35 | C15H24 |
| | 3 | cis-.alpha.-Bisabolene | 14.81 | 4.92 | | |
| | 4 | (−)-.beta.-Sesquiphellandrene | 15.023 | 24.04 | 204.35 | C15H24 |
| | 5 | 4-(2,2-Dimethyl-6-methylenecyclohexyl)butanal | 16.13 | 0.89 | 194.3132 | C13H22O |
| | 6 | ar-Turmerone | 16.695 | 1.85 | 216.32 | C15H20O |
| | 7 | Turnerone | 16.747 | 16.74 | 218.3346 | C15H22O |
| | 8 | Caryophyllene | 17.136 | 9.65 | 204.36 | C15H24 |
| | 9 | Cyclopentane | 17.488 | 1.19 | 70.13 | C5H10 |
| | 10 | Cyclohexane, 1-methyl-2,4-bis(1-methylethenyl)- | 18.074 | 2.04 | 204.35 | C15H24 |

The effects of different laser exposure times on the production of secondary metabolites in C. longa rhizomes was investigated (Table 2). The amounts of bisdemethoxycurcumin, demethoxycurcumin, and curcumin present in the ethanolic extracts were quantified using high-performance liquid chromatography (HPLC) by comparing the standard curve prepared using a series of bisdemethoxycurcumin, demethoxycurcumin, and curcumin solutions with known concentrations. The two Laser treatments significantly increased the bisdemethoxycurcumin, and curcumin levels as compared to the control treatment (Table 2). On the other hand, the exposure of rhizome to laser for 10 and 15 minutes resulted in a significant decrease in demethoxycurcumin levels compound as compared to control (Table 2).

TABLE 2

Effects of two Laser treatments (exposure times; 10 and 15 minutes) on bisdemethoxycurcumin, demethoxycurcumin, and curcumin (ug/mL) accumulation in C. longa in the second season.

| laser Treatments (min) | Bisdemethoxy-curcumin (µg/mL) | Demethoxy-curcumin (µg/mL) | Curcumin (µg/mL) |
|---|---|---|---|
| Control | 70.761b* | 80.403a | 327.249a |
| 10 | 100.495a | 60.779c | 220.853b |
| 15 | 101.191a | 70.682b | 380.803a |

*Means followed by the same letter within a column are not significantly different at a 0.05 level of probability, according to the LSD test.

Example 2

Antimicrobial bioassay results of extracts derived from laser-treated rhizome are presented in Table 3. Each of the mean measurements was obtained from the average of nine replicate plates. The test solution positive control was 10 µg Imipenem. Three Curcuma longa extracts (5 mg/L) were prepared from ethanolic rhizome extracts as well as the control.

TABLE 3

| | Inhibition Zone (mm) ± Standard deviation | | | |
|---|---|---|---|---|
| Test Solution | S. aureus | E. coli | MRSA | Bacillus sp. |
| Curcuma longa extract (control) | $10^{c*} \pm 1$ | $8^d \pm 2$ | $7^c \pm 2$ | $10^f \pm 1$ |
| Curcuma longa extract (Laser10) | $13^b \pm 2$ | $11^c \pm 1$ | $11^{ab} \pm 1$ | $14^c \pm 2$ |
| Curcuma longa extract (laser15) | $9^f \pm 2$ | $13^b \pm 1$ | $15^b \pm 1$ | $17^b \pm 2$ |
| Imipenem 10 µg (positive control) | $18^a \pm 1$ | $20^a \pm 2$ | $25^a \pm 1$ | $19^a \pm 1$ |

*Means followed by the same letter within a column are not significantly different at 0.05 level of probability according to L.S.D. test.

It is to be understood that the compositions and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of enhancing active components in *Curcuma longa*, the method comprising:
   providing a *Curcuma longa* rhizome;
   irradiating the *Curcuma longa* rhizome with a laser; and
   providing an ethanolic extract of the laser irradiated *Curcuma longa* rhizome to obtain a *Curcuma longa* rhizome extract of increased amounts of active ingredients of alpha-curcumene, (-)-zingiberene, caryphyllene, and beta sesquiphellandrene as compared to that of the *Curcuma longa* rhizome, and wherein the *Curcuma longa* rhizome is irradiated with a laser having a wavelength of about 632 nm and a density power of about 5.5 mW/mm$^2$.

2. The method of claim 1, wherein the *Curcuma longa* rhizome is irradiated for about 1 to about 15 minutes.

3. The method of claim 2, wherein the *Curcuma longa* rhizome is irradiated for about 10 or about 15 minutes.

4. The method of claim 1, wherein the *Curcuma longa* rhizome is irradiated for more than about 15 minutes.

5. The method of claim 1, wherein the *Curcuma longa* rhizome extract has about 101 μg/mL of bisdemethoxycurcumin, about 70 μg/mL of demethoxycurcumin, and about 380 μg/mL of curcumin.

6. The method of claim 1, wherein the *Curcuma longa* rhizome extract has at least an about 1.67 fold increase in alpha-curcumene as compared to that of the *Curcuma longa* rhizome.

* * * * *